United States Patent
Gu (10) Patent No.: US 6,606,579 B1
(45) Date of Patent: *Aug. 12, 2003

(54) METHOD OF COMBINING SPECTRAL DATA WITH NON-SPECTRAL DATA IN A PRODUCE RECOGNITION SYSTEM

(75) Inventor: Yeming Gu, Suwanee, GA (US)

(73) Assignee: NCR Corporation, Dayton, OH (US)

( * ) Notice: Subject to any disclaimer, the term of this patent is extended or adjusted under 35 U.S.C. 154(b) by 171 days.

This patent is subject to a terminal disclaimer.

(21) Appl. No.: 09/640,033

(22) Filed: Aug. 16, 2000

(51) Int. Cl.$^7$ .............................. G06F 17/60
(52) U.S. Cl. ................. 702/181; 702/179; 235/385
(58) Field of Search ................ 702/180, 181, 702/81, 82, 83, 84, 27, 28, 30, 76, 127, 179, 183, FOR 115–118, FOR 131–132, FOR 137, FOR 139, FOR 141; 235/383, 462.06, 462.11, 462.14, 385; 382/110, 190, 181; 356/326, 328, 302, 303, 306, 419, 402, 408; 705/20, 23; 250/226

(56) References Cited

U.S. PATENT DOCUMENTS

| | | | |
|---|---|---|---|
| 4,693,330 A | | 9/1987 | Uchimura et al. ....... 177/25.14 |
| 5,166,755 A | | 11/1992 | Gat ............................ 356/419 |
| 5,546,475 A | * | 8/1996 | Bolle et al. ................. 382/190 |
| 5,649,070 A | * | 7/1997 | Connell et al. ............... 706/14 |
| 5,867,265 A | | 2/1999 | Thomas ....................... 356/328 |
| 6,069,696 A | * | 5/2000 | McQueen et al. .......... 356/326 |
| 6,155,489 A | * | 12/2000 | Collins et al. ......... 235/462.01 |
| 6,260,023 B1 | * | 7/2001 | Seevers et al. ............... 705/20 |
| 6,313,917 B1 | * | 11/2001 | Tang et al. ................. 356/402 |
| 6,332,573 B1 | * | 12/2001 | Gu et al. ............... 235/462.06 |
| 6,409,085 B1 | * | 6/2002 | Gu ........................ 235/462.11 |
| 6,471,125 B1 | * | 10/2002 | Addy ......................... 235/385 |

* cited by examiner

Primary Examiner—Hal Wachsman
(74) Attorney, Agent, or Firm—Paul W. Martin

(57) ABSTRACT

A method of combining spectral data with non-spectral data which uses a defined distance measure of likeness (DML) value and conditional probabilities. The method includes the steps of collecting the spectral and non-spectral data for the produce item, determining DML values between the spectral and the non-spectral data and reference produce data for a plurality of types of produce items, determining conditional probability densities for all of the types of produce items using the DML values, combining the conditional probability densities to form a combined conditional probability density, and determining probabilities for the types of produce items from the combined conditional probability density.

12 Claims, 7 Drawing Sheets

METHOD OF COMBINING SPECTRAL DATA WITH NON-SPECTRAL DATA IN A PRODUCE RECOGNITION SYSTEM

CROSS-REFERENCE TO RELATED APPLICATIONS

"A Produce Data Collector And A Produce Recognition System", filed Nov. 10, 1998, invented by Gu, and having a U.S. Ser. No. 09/189,783, now U.S. Pat. No. 6,332,573;

"System and Method of Recognizing Produce Items Using Probabilities Derived from Supplemental Information", filed Jul. 10, 2000, invented by Kerchner, and having a U.S. Ser. No. 09/612,682; "Method of Recognizing Produce Items Using Checkout Frequency", filed Aug. 16, 2000, invented by Gu, and having a U.S. Ser. No. 09/640,032, now issued as U.S. Pat. No. 6,409,085; and "Produce Texture Data Collecting Apparatus and Method", filed Aug. 16, 2000, invented by Gu, and having a U.S. Ser. No. 09/640,0254 pending.

Background of the Invention

The present invention relates to product checkout devices and more specifically to a method of combining spectral data with non-spectral data in a produce recognition system.

Bar code readers are well known for their usefulness in retail checkout and inventory control. Bar code readers are capable of identifying and recording most items during a typical transaction since most items are labeled with bar codes.

Items which are typically not identified and recorded by a bar code reader are produce items, since produce items are typically not labeled with bar codes. Bar code readers may include a scale for weighing produce items to assist in determining the price of such items. But identification of produce items is still a task for the checkout operator, who must identify a produce item and then manually enter an item identification code. Operator identification methods are slow and inefficient because they typically involve a visual comparison of a produce item with pictures of produce items, or a lookup of text in table. Operator identification methods are also prone to error, on the order of fifteen percent.

A produce recognition system is disclosed in the cited co-pending application, U.S. Ser. No. 09/189,783, now U.S. Pat. No. 6,332,573. A produce item is placed over a window in a produce data collector, the produce item is illuminated, and the spectrum of the diffuse reflected light from the produce item is measured. A terminal compares the spectrum to reference spectra in a library. The terminal determines candidate produce items and corresponding confidence levels and chooses the candidate with the highest confidence level. The terminal may additionally display the candidates for operator verification and selection.

Increases in speed and accuracy are important in a checkout environment. It would be desirable to improve the speed and accuracy of the produce recognition process by supplementing spectral data with additional information helpful to recognition. Types of data which could potentially be used to improve identification include texture data, size and shape data, weight and density data, and brightness data.

Since each data type describes a different physical attribute of an object, combining them mathematically is difficult and non-trivial. Specifically, the spectral data may consist of dozens of variables, each corresponding to a single color band, while weight and brightness, for example, may each be represented by a single variable.

Therefore, it would be desirable to provide a method of combining spectral data with non-spectral data in a produce recognition system.

SUMMARY OF THE INVENTION

In accordance with the teachings of the present invention, a method of combining spectral data with non-spectral data in a produce recognition system is provided.

A method is presented for using a defined distance measure of likeness (DML) algorithm and Bayes Rule to compute a probability of an unknown object being of a given class $C_i$. In particular, the DML algorithm allows the projection of any data type into a one-dimensional space, thus simplifying the multivariate conditional probability density function into an univariate function. The conditional probability densities from spectral and non-spectral data types are combined together with a priori probabilities through Bayes Rule to provide a probability estimate for each class. The resulting combination provides a statistically self-consistent estimate of the a posteriori probability for each class. A posteriori Probability values can then be used to rank the classes and to determine a subset of the most likely classes.

The method includes the steps of collecting the spectral and non-spectral data for the produce item, determining DML values between the spectral and the non-spectral data and reference produce data for a plurality of types of produce items, determining conditional probability densities for all of the types of produce items using the DML values, combining the conditional probability densities to form a combined conditional probability density, and determining probabilities for the types of produce items from the combined conditional probability density.

It is accordingly an object of the present invention to provide a method of combining spectral data with non-spectral data in a produce recognition system.

It is another object of the present invention to improve the speed and accuracy of produce recognition.

It is another object of the present invention to provide a produce recognition system and method.

It is another object of the present invention to provide a produce recognition system and method which combining spectral data with non-spectral data.

It is another object of the present invention to provide a produce recognition system and method which combines spectral data with non-spectral data using a distance measure of likeness (DML) value.

It is another object of the present invention to provide a produce recognition system and method which combines spectral data with non-spectral data and which identifies produce items by sorting the distance measure of likeness (DML) values in ascending order and choosing the item with smallest distance as the most likely identification.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

DETAILED DESCRIPTION OF THE PREFERRED EMBODIMENT

Figure 1:
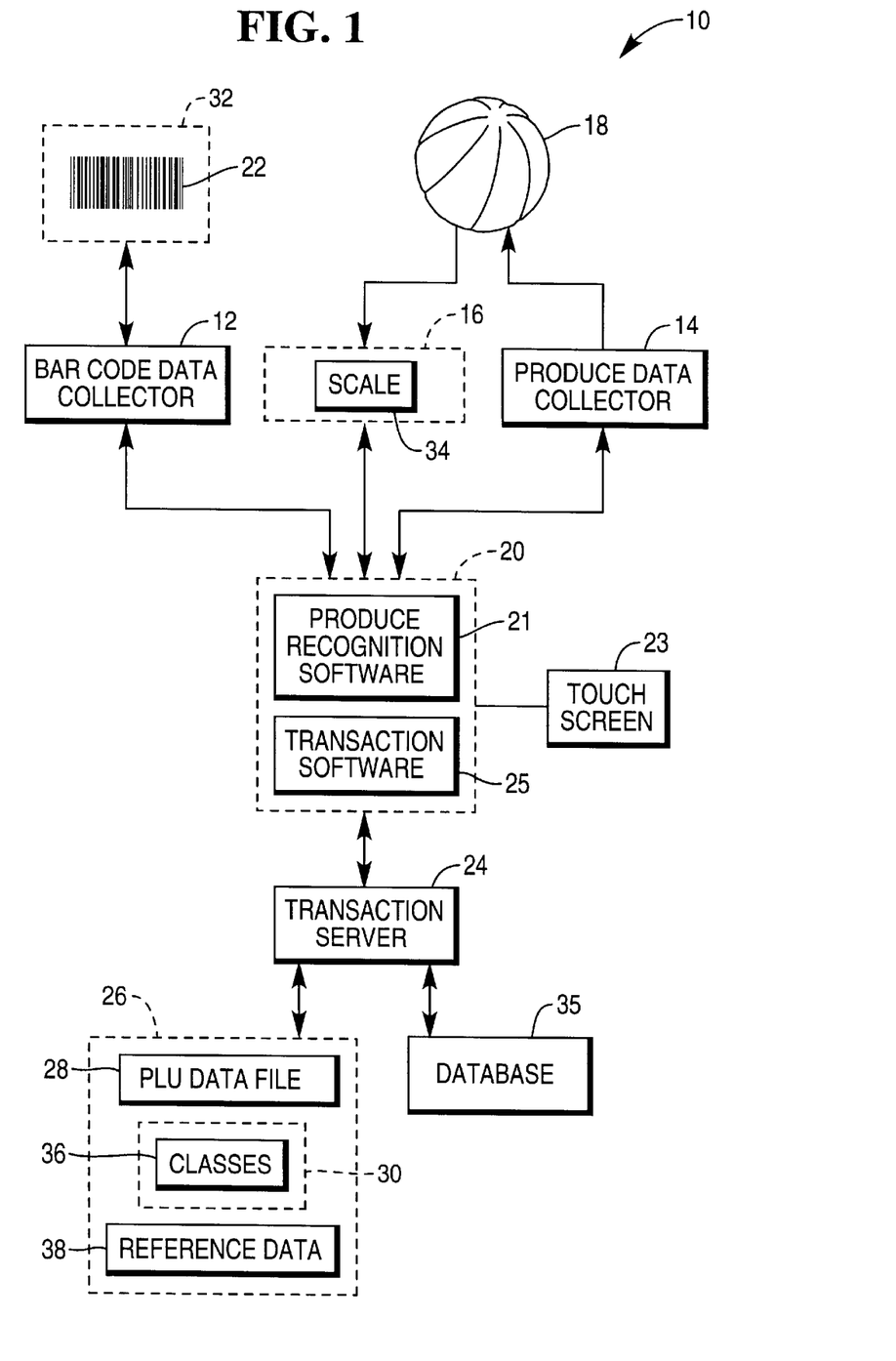
FIG. 1 is a block diagram of a transaction processing system including a produce recognition system.

Referring now to FIG. 1, transaction processing system 10 includes bar code data collector 12, spectral produce data collector 14, and non-spectral produce data collector 16.

Bar code data collector 12 reads bar code 22 on merchandise item 32 to obtain an item identification number, also know as a price look-up (PLU) number, associated with item 32. Bar code data collector 12 may be any bar code data collector, including an optical bar code scanner which uses laser beams to read bar codes. Bar code data collector 12 may be located within a checkout counter or mounted on top of a checkout counter.

Figure 2:
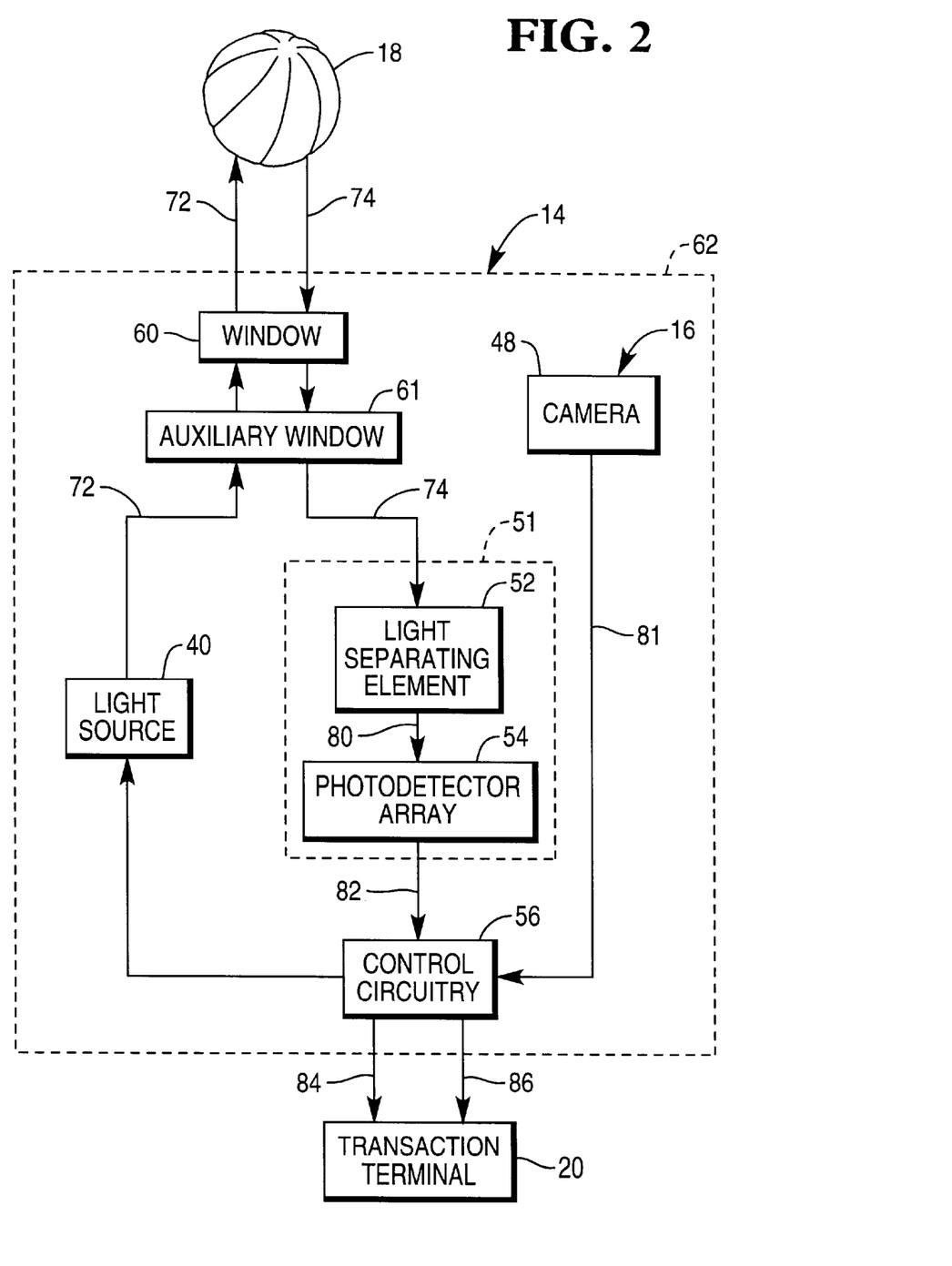
FIG. 2 is a block diagram of a type of spectral data collector.

Spectral data collector 14 collects spectral data from produce item 18. Spectral data collector 14 preferably includes spectrometer 51 (FIG. 2)

Non-spectral data collector 16 collects data such as size data, shape data, surface texture data, weight data, and aromatic data. Non-spectral data collector 16 includes components necessary to capture one or more of such types of data.

For example, non-spectral data collector 16 may include scale 34. Scale 34 provides weight information which not only helps determine the total price of produce item 18, but also helps distinguish produce item 18 from other produce items.

As another example, non-spectral data collector 16 may include camera 48 (FIG. 2) for providing size, shape, and surface texture data.

Components of non-spectral data collector 16 may reside with spectrometer 51 of spectral data collector 14. For example, camera 48 may reside in housing 62 (FIG. 2) with spectrometer 51.

Non-spectral data may also include a priori or supplemental probabilities, such as those derived from customer shopping histories. Shopping histories may be collected as part of a customer loyalty program.

Database 35 stores information used to determine a prior probabilities. For this purpose, database 35 may include a data warehousing system. Database 35 is accessible to transaction server 24 and may be stored within storage medium 26. Database 35 may alternatively be stored elsewhere, for example, at a centralized store management location.

Classification library 30 contains reference data from previously collected and processed spectral and non-spectral produce data.

Reference data 38 is device-dependent data for data reduction steps. For example, data 38 includes calibration information and pixel-to-wavelength mapping and interpolation information used in the data reduction process.

During a transaction, spectral data collector 14 may be self-activated when produce item 18 blocks ambient light from entering window 60 (FIG. 2), or initiated by placement of produce item 18 on scale 34 or by operator commands recorded by touch screen 23 (or other input device).

Bar code data collector 12 and spectral data collector 14 operate separately from each other, but may be integrated together. Bar code data collector 12 works in conjunction with transaction terminal 20 and transaction server 24.

Scale 34 may also work in connection with bar code data collector 12, but may be designed to operate and be mounted separately.

In the case of bar coded items, transaction terminal 20 obtains the item identification number from bar code data collector 12 and retrieves a corresponding price from PLU data file 28 through transaction server 24.

In the case of non-bar coded produce items, transaction terminal 20 executes produce recognition software 21 which obtains spectral characteristics of produce item from spectral data collector 14, non-spectral characteristics of produce item from non-spectral data collector 48 and/or database 35, identifies produce item 18 by comparing produce data in classification library 30 with collected produce data and non-spectral data with reference non-spectral data, retrieves an item identification number from classification library 30 and passes it to transaction software 25, which obtains a corresponding price from PLU data file 28.

Each sample of spectral and non-spectral data represents an instance to be processed by produce recognition software 21.

In an alternative embodiment, identification of produce item 18 may be handled by transaction server 24. Following identification, transaction server 24 obtains a price for produce item 18 and forwards it to transaction terminal 20.

Storage medium 26 preferably includes one or more hard disk drives. PLU data file 28 and classification library 30 are stored within storage medium 26, but either may also be located instead at transaction terminal 20, or bar code data collector 12. Reference data 38 is also stored within storage medium 26, but as device-dependent data, they may also be stored on board the relevant devices, e.g., in flash memory chips in spectral and non-spectral data collectors 16 and 18. Upon system startup, produce recognition software 21 extracts reference data 38 from hardware devices and updates that data within storage medium 26.

To assist in proper identification of produce items, produce recognition software 21 may additionally display candidate produce items for operator verification. Produce recognition software 21 preferably arranges the candidate produce items in terms of probability of match and displays them as text and/or color images on an operator display of transaction terminal 20, such as touch screen 23. The operator may accept the most likely candidate returned by or override it with a different choice.

Figure 3:
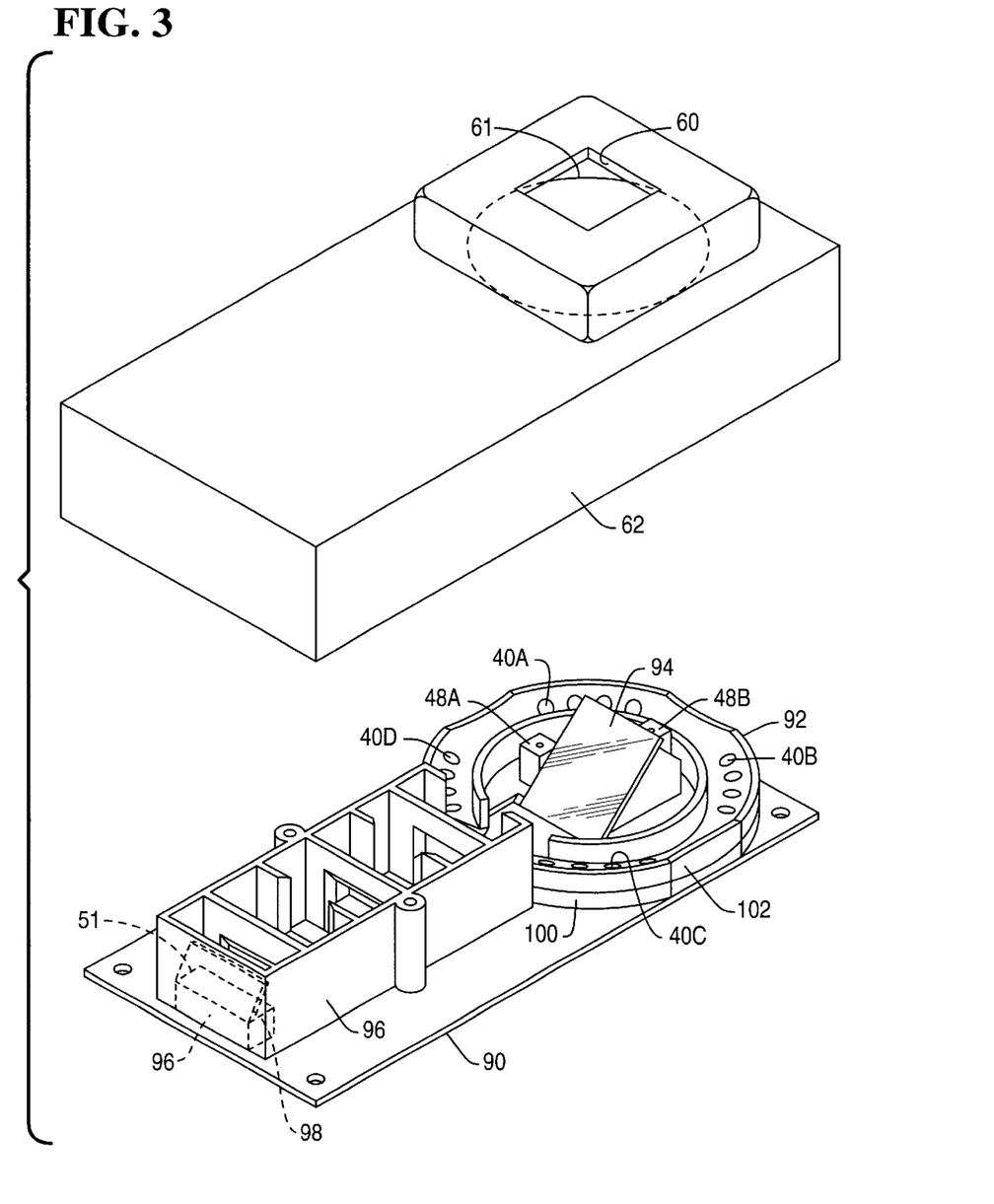
FIG. 3 is a detailed view of the spectral data collector of FIG. 2.

Turning now to FIGS. 2 and 3, an example spectral data collector 14 which relies on spectroscopic analysis is illustrated. Other types of spectral data collectors are also envisioned.

This example spectral data collector 14 is combined with camera 48, an example of a non-spectral data collector 16. However, separation of data collector 14 and camera 48 is also envisioned.

Example spectral data collector 14 primarily includes light source 40, spectrometer 51, control circuitry 56, transparent window 60, and housing 62.

Light source 40 produces light 72. Light source 40 preferably produces a white light spectral distribution, and preferably has a range from four hundred 400 nm to 700 nm, which corresponds to the visible wavelength region of light.

Light source 40 preferably includes one or more light emitting diodes (LEDs). A broad-spectrum white light producing LED, such as the one manufactured by Nichia Chemical Industries, Ltd., is preferably employed because of its long life, low power consumption, fast turn-on time, low operating temperature, good directivity. Alternate embodiments include additional LEDs having different colors in narrower wavelength ranges and which are preferably used in combination with the broad-spectrum white light LED to even out variations in the spectral distribution and supplement the spectrum of the broad-spectrum white light LED.

Other types of light sources 40 are also envisioned by the present invention, although they may be less advantageous than the broad spectrum white LED. For example, a tungsten-halogen light may be used because of its broad spectrum, but it has very limited life and produces more heat.

A plurality of different-colored LEDs having different non-overlapping wavelength ranges may be employed, but may provide less than desirable collector performance if gaps exist in the overall spectral distribution.

Spectrometer 51 includes light separating element 52 and photodetector array 54.

Light separating element 52 splits light 76 in the preferred embodiment into light 80 of a continuous band of wavelengths. Light separating element 52 is preferably a linear variable filter (LVF), such as the one manufactured by Optical Coating Laboratory, Inc., or may be any other functionally equivalent component, such as a prism or a grating.

Photodetector array 54 produces waveform signals 82 containing spectral data. The pixels of the array spatially sample the continuous band of wavelengths produced by light separating element 52, and produce a set of discrete signal levels. Photodetector array 54 is preferably a photodiode array, or a complimentary metal oxide semiconductor (CMOS) array, but could be a Charge Coupled Device (CCD) array.

Control circuitry 56 controls operation of spectral data collector 14 and produces digitized produce data waveform signals 84. For this purpose, control circuitry 56 includes an analog-to-digital (A/D) converter. A twelve bit A/D converter with a sampling rate of 22–44 kHz produces acceptable results.

Transparent window 60 is mounted above auxiliary transparent window 61. Windows 60 and 61 include an antireflective surface coating to prevent light 72 reflected from windows 60 and 61 from contaminating reflected light 74.

Housing 62 contains light source 40, spectrometer 51, photodetector array 54, control circuitry 56, auxiliary transparent window 61, and transparent window 60. Housing 62 additionally contains camera 48.

Camera 48 captures a number of types of non-spectral data which is used by produce recognition software 21 to determine size, shape, and texture information about produce item 18. Control circuitry 56 processes the non-spectral data along with spectral data.

With reference to FIG. 3, spectral data collector 14 is illustrated in more detail.

Spectral data collector 14 additionally includes printed circuit board 90, light source assembly 92, turning mirror 94, stray light baffle 96, and turning mirror 98.

Printed circuit board 90 contains control circuitry 56, spectrometer 51, light source assembly 92, turning mirror 94, stray light baffle 96, and turning mirror 98. Printed circuit board 90 fastens to housing 62.

Light source assembly 92 includes light source 40, lower light source mount 100, and upper light source mount 102.

Light source 40 preferably includes a number of white LEDs which are arranged close to window 60 and in direct line of sight of window 60. Light source mount 92 is designed such that each individual LED is pointed at the top surface of window 60 so that there is uniform luminosity over the entire top surface of window 60 for illuminating produce item 18. The LEDs are spectrally matched in groups, and their placement and orientation achieves optimal uniformity in both spectrum and luminosity across the illuminated surface area.

The illustrated embodiment includes sixteen white LEDs arranged in four groups 40A, 40B, 40C, and 40D of four LEDs on four sides of lower light source mount 100. Other arrangements are also envisioned by the present invention, such as two or four groups of four and eight LEDS. To achieve higher system efficiency, LEDs with a narrow, concentrated beam are preferred. The actual number of LED's depends on the overall system efficiency requirement. Fewer LED's may be needed if the longer integration time of the detector array is acceptable.

Lower light source mount 100 is generally circular in shape. This arrangement supports the LEDs in the preferred arrangement and orientation. Lower light source mount 100 connects mechanically and electrically to printed circuit board 90.

Upper light source mount 102 is also generally circular in shape and connects mechanically in mating relationship to lower light source mount 100. Upper light source mount 102 mechanically holds the LEDs in a preferred orientation for even illumination across the area of window 60.

Turning mirror 94 routes reflected light 74 from produce item 18 through stray light baffle 96 towards turning mirror 98. Turning mirror 94 is mounted at about a forty-five degree.

Camera 48 includes a number of image capture devices, 48A and 48B, which are mounted adjacent turning mirror 94. Image capture devices 48A and 48B are preferably pinhole cameras for simplicity.

Stray light baffle 96 minimizes the amount of stray light which reaches spectrometer 51. Stray light baffle 96 effectively establishes an entrance cone from photodetector 54 through window 60. Only light oriented inside the solid angle defined by this cone can reach photodetector 54.

Turning mirror 98 directs reflected light 74 to spectrometer 51. Turning mirror 98 is mounted at about a forty-five degree angle.

In operation, an operator places produce item 18 on window 60. Control circuitry 56 turns on light source 40. Light separating element 52 separates reflected light 74 into different wavelengths to produce light 80 of a continues band of wavelengths. Photodetector array 54 produces waveform signals 82 containing spectral data. Camera 48 produces non-spectral data signals 81. Control circuitry 56 produces digitized spectral data signals 84 and non-spectral data signals 86 which it sends to transaction terminal 20. Control circuitry 56 turns off light source 40 and goes into a wait state.

Transaction terminal 20 compares the collected produce data, including digitized spectral data signals 84 and non-spectral data 86, to pre-collected produce data stored within classification library 30 to identify produce item 18.

Classification library 30 is derived from previously collected and processed produce data. In general, a classification library contains information of various classes 36, with each class 36 representing an identifiable produce item. For example, bananas, golden delicious apples, and white potatoes are three different classes. Each class 36 is uniquely identified by a class number.

More specifically, library 30 preferably includes typical instances and other related distance measure of likeness (DML) parameters, and the probability density distribution as a function of the DML parameters. Library 30 may additionally include a priori or supplemental probabilities. It may also include all the instances to allow easy update of all statistical parameters when new instances are added to (or old instance dropped from) library 30.

If a class number is associated with more than one PLU number, the additional PLU numbers represent a produce item which is similar except for different non-classifiable features. These features include cultivation methods (regular verses organic), ripening methods (regular verses vine-ripened or tree-ripened), seeded verses seedless, etc. Since non-classifiable features are normally not discernable by visually examining produce items, their identification will have to be accomplished using additional means, such as stickers, color-coded rubber bands, etc.

There are two ways to process produce items with non-distinguishable features. In the first method, a class with multiple PLU numbers is expanded into multiple choices when presented to the operator in the user interface, and the operator identifies a produce item 18 by its non-distinguishable features.

A second method involves additional operator input. After the operator selects the correct class, produce recognition software 21 prompts the operator to enter non-distinguishable features for produce item 18, e.g., through a pop-up window on a graphic user interface.

In either case, produce recognition software 21 computes a DML distance and a class-conditional probability density as a function of the DML distance during the recognition process. Produce recognition software 21 may additionally determine the a posteriori probability that a given instance is within a class. The class with the highest a posteriori probability is the most likely class.

Distance Measure of Likeness

Produce recognition software 21 uses a DML algorithm to compute the probability of an unknown object being of a given class $C_i$. Produce recognition software 21 compares DML values between an unknown instance of data and all classes 36 within library 30.

The DML algorithm allows the projection of any data type into a one-dimensional space, thus simplifying the multi-variate conditional probability density function into an univariate function.

While the sum of squared difference (SSD) is the simplest measure of distance between an unknown instance and instances of known items, the distance between an unknown instance and a class of instances is most relevant to the identification of unknown instances. A distance measure of likeness (DML) value provides a distance between an unknown instance and a class, with the smallest DML value yielding the most likely candidate.

In more detail, each instance is a point in the N-dimensional space, where N is the number of parameters that are used to describe the instance. The distance between points $P_1(x_{11}, x_{21}, \ldots, x_{N1})$ and $P_2(x_{12}, x_{22}, \ldots, x_{N2})$ is defined as $$d(P_1, P_2) = \sqrt{\sum_{i=1}^{N} (x_{i2} - x_{i1})^2} . \tag{1}$$

The distance between two instances, $d(P_1, P_2)$, measures how far apart the two instances are in the N-dimensional space. In the ideal case of well-defined classes 36, i.e., each class is represented by a single point in the N-dimensional space, produce identification is reduced to point matching: an instance P is identified as item j only if $d(P, P_j) = 0$.

In reality, there are always measurement errors due to instrumental noise and other factors. No two items of the same class are identical, and for the same item, the color and appearance changes over its surface area. The variations of orientation and distance of produce item 18 relative to window 60 further affect the measurements. All these factors contribute to the spreading of instance data in the N-dimensional space.

In a supermarket, a large number of instance points are measured from all the items of a class. There are enough instances from all items for all instance points to be spread in a practically definable volume in the N-dimensional space or for the shape and size of this volume to completely characterize the appearances of all the items of the class. The shape of this volume may be regular, like a ball in three dimensions, and it may be quite irregular, like a dumbbell in three dimensions.

Now if the unknown instance P happens to be in the volume of a particular class, then it is likely to be identifiable as an item of the class. There is no certainty that instance P is identifiable as an item in the class if there are other classes 36 with their volumes overlapping this volume. So instance P could be simultaneously in the volumes of several classes 36. Therefore, the simple distance measure $d(P_1, P_2)$ above is not the best identification tool for such cases, since a class is characterized by a volume in N-dimensional, not by points.

A class is not only best described in N-dimensional space, but also is best described statistically, i.e., each instance is a random event, and a class is a probability density distribution in a certain volume in N-dimensional space.

Figure 4:
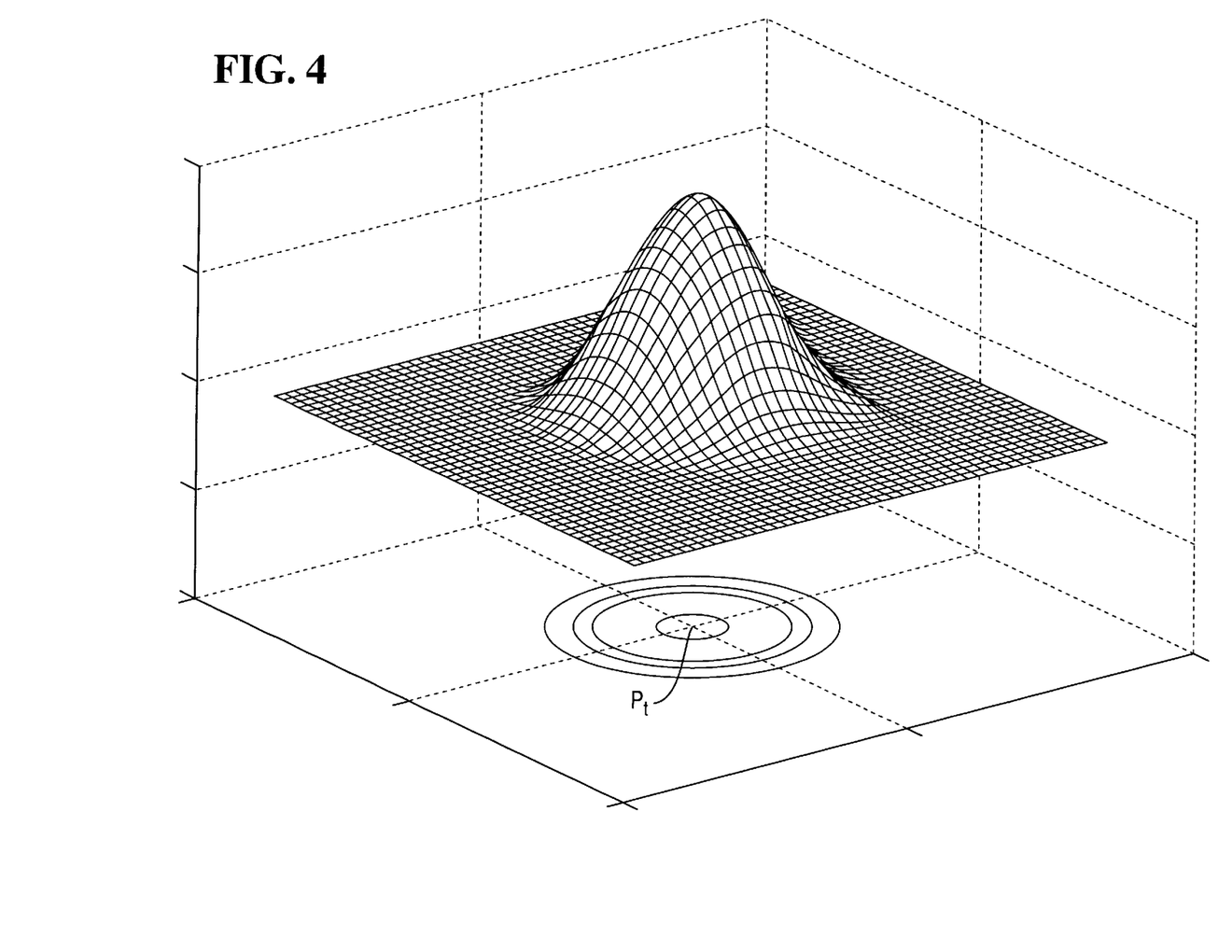
FIG. 4 is an illustration of a probability density distribution of random samples on a two-dimensional plane.

As an example, consider randomly sampling items from a large number of items within the class "Garden Tomatoes". The items in this class have relatively well defined color and appearance: they are all red, but there are slight color variations from item to item, and even from side to side of the same item. However, compared to other classes 36, such as "Apples", there are much fewer item-to-item color variations. Since a typical tomato has a color which is "tomato red", a typical instance, $P_t$, associated with the typical tomato will be at or near the center of the N-dimensional volume of the class "Garden Tomatoes". Since items in the class have only slight color variations, most instances from a random sampling will be close to this typical instance $P_t$. Further away from instance $P_t$, fewer points will be found. Schematically this is illustrated in FIG. 4, where the probability density for finding a random event on the two-dimensional plane is plotted as a mesh surface and also contoured at the bottom of the figure. The falling-off of probability density for a given class can be verified by looking at the histogram of the distances between instance $P_t$ and all the instance points that are randomly sampled for the class.

It is difficult to imagine, much less to illustrate, the relative positions and overlapping of classes 36 in N-dimensional space, where N is larger than three. So the following discussion starts in two-dimensional space and extends to higher dimensions.

Figure 5:
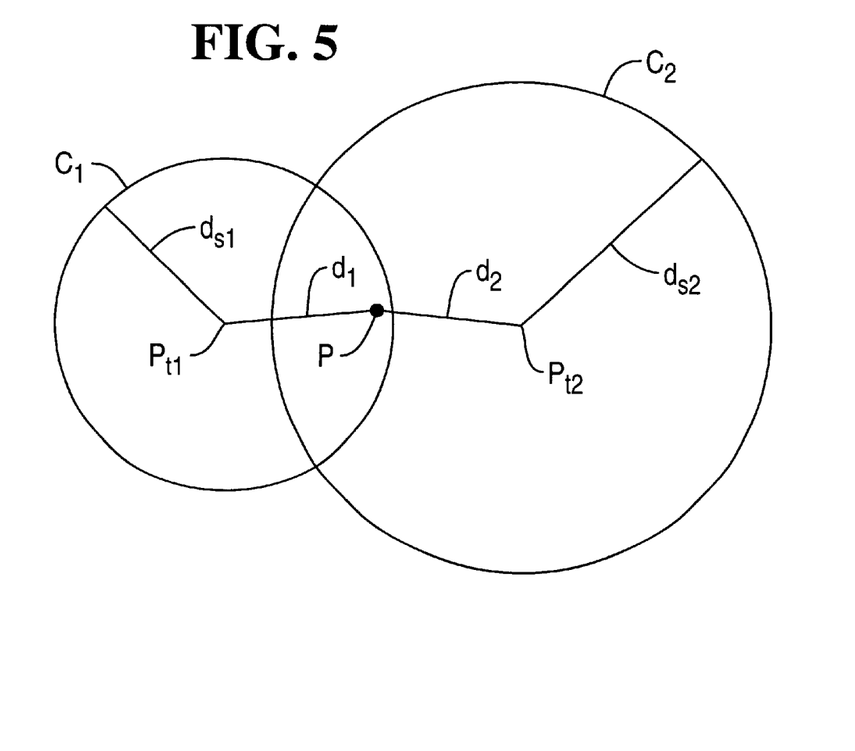
FIG. 5 is an illustration of symmetric two-dimensional probability density distributions for two classes.

A first ideal example in two-dimensional space is shown in FIG. 5. This example assumes that each class can be represented by a symmetric probability distribution, i.e., all contour lines in FIG. 4 are circles. Without knowing the actual shape of the distribution function (e.g., whether it is Gaussian or non-Gaussian), the distribution can be characterized by a typical distance scale $d_s$, which is a radius of one of the contour lines in FIG. 4. It can be regarded as a distance from the typical instance beyond which the probability density is significantly lower than inside it.

An unknown instance P happens to be in the overlapping area of two classes, $C_1$ and $C_2$. The unknown instance P could belong to either class. Using a simple distance measure does not help identify the likely class, since instance P is about equal distances $d_1$ and $d_2$ away from typical instances $P_{t1}$, and $P_{t2}$. However, under the assumption that the probability density is inversely proportional to distance relative to distance scale, instance P is more likely to belong to class $C_2$ than class $C_1$, since $$\frac{d_2}{d_{s2}} < \frac{d_1}{d_{s1}}. \tag{2}$$

Relative to the respective distance scale, instance P is closer to the typical instance $P_{t2}$ of class $C_2$ than to the Far typical instance $P_{t1}$ of class $C_1$.

Figure 6:
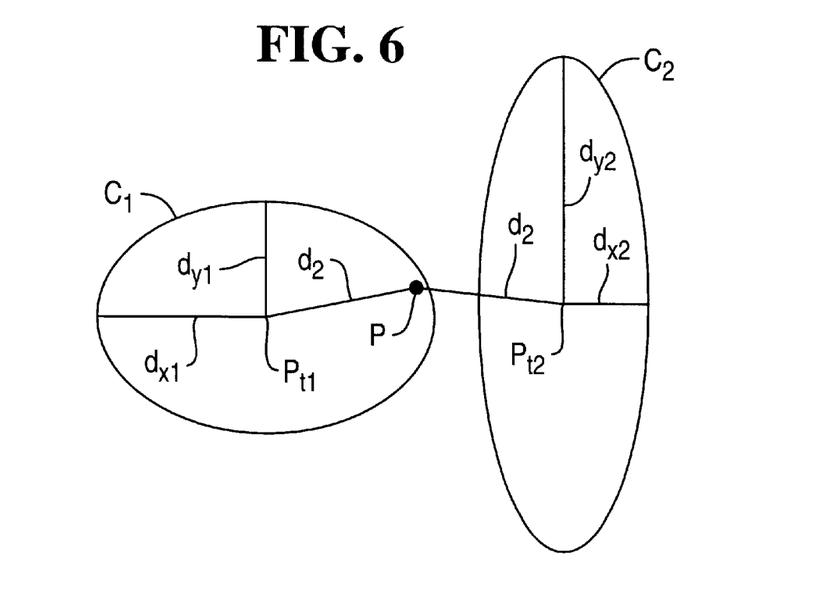
FIG. 6 is an illustration of asymmetric two-dimensional probability density distributions for two classes of produce items.

A second example in two-dimensional space is shown in FIG. 6. This example illustrates an asymmetric distribution, since the distribution may not always be symmetric. For example, if the distribution is due to measurement error, the error might be larger near the red end of the spectrum than the blue end. In fact, the intrinsic color variation of most classes 36 is non-uniform across the spectral range. For asymmetric distributions, a distance scale for the x- and y-dimensions must be defined.

Although the relative positions of $P_{t1}$, $P_{t2}$, and P are the same as in FIG. 5, the distribution of class $C_2$ is much narrower in x-dimension than the distribution of class $C_1$. Thus, instance P is much more likely to belong to class $C_1$ than class $C_2$.

A generalized distance measure for symmetric and asymmetric distributions in two-dimensional space is herein defined. This distance measure is a Distance Measure of Likeness (DML) for an unknown instance P(x, y) relative to a class $C_j$:

$$D_j = \sqrt{\frac{(x - x_{tj})^2}{d_{xj}^2} + \frac{(y - y_{tj})^2}{d_{yj}^2}}, \tag{3}$$

where $P_{tj}(x_{tj}, y_{tj})$ is a typical instance of class $C_j$, and $d_{xj}$ and $d_{yj}$ are typical distance scales for class $C_j$ in x- and y-dimensions, respectively.

The following DML definition is extended to N-dimensional space:

$$D_j = \sqrt{\sum_{i=1}^{N} \frac{(x_i - x_{tij})^2}{d_{ij}^2}}, \tag{4}$$

where $P(x_1, x_2, \ldots, x_N)$ is an unknown instance, $P_{tj}(x_{t1j}, x_{t2j}, \ldots, x_{tNj})$ is a typical instance for the j-th class, $d_{ij}$ is the distance scale in i-th dimension, and where $D_j$ is the distance measure between instance P and the class defined by typical instance $P_{tj}$ and the corresponding distance scales. In comparing unknown instance P with a library of typical instances $P_{tj}$, the class with the smallest DML value $D_j$ corresponds to the most likely identification.

Before a DML value may be calculated, the typical instance and the related distance scales must be determined. If each class has a relatively well-defined color and the instance-to-instance variations are mostly random, then the typical instance is well approximated by the average instance:

$$P_{tj}(x_{t1j}, x_{t2j}, \ldots, x_{tNj}) \approx \frac{\sum_{k=1}^{n_j} P_{jk}(x_{1jk}, x_{2jk}, \ldots x_{Njk})}{n_j}, \tag{5}$$

where each class in library 34 is represented by a large number of randomly sampled instances, each instance is measured by N parameters, $n_j$ is the number of instances in the j-th class, and the j-th class in library 34 is represented by a group of $n_j$ points in N-dimensional space:

$$P_{jk}(x_{1jk}, x_{2jk}, \ldots, x_{Njk}), k=1, 2, \ldots, n_j. \tag{6}$$

Each instance point $P_{jk}$ is actually a vector, and the sum $$\sum_{k=1}^{n_j} P_{jk}(x_{1jk}, x_{2jk}, \ldots, x_{Njk}) \tag{7}$$

is a vector sum. Thus, the distance scale for i-th dimension can be defined as the root-mean-square (rms) deviation of the i-th parameter:

$$DML \equiv d_{ij} = \sqrt{\frac{\sum_{k=1}^{n_j}(x_{ijk} - x_{tik})^2}{n_j}}. \tag{8}$$

Class-conditional Probability Density Function

The conditional probability density function of the spectral data for a given class (containing classifiable items) can be modeled and computed using the DML distance value.

Captured spectral data is discrete data defined by many small wavelength bands. A spectrometer may record color information in dozens or even hundreds of wavelength bands. However, since diffuse reflection has a continuous and relatively smooth spectrum, about sixty equally-spaced wavelength bands in the 400–700 nm may be adequate. The optimal number of wavelength bands depends on the application requirement and the actual resolution of the spectrometer. Let's define $N_s$ as the number of spectral bands, i.e., there are $N_s$ discrete spectral components for each measurement.

Assuming that the spectral variation of the diffuse reflection from a given class of objects is due to intrinsic color variation and some relatively small measurement error, then for a given class, the DML value provides a distance measure in a N-dimensional space. If we model the conditional probability density with the multivariate normal density function, due to the definition of DML we have $$p(x \mid C_i) = \frac{1}{\sqrt{2\pi}} e^{(-\frac{1}{2}D_i^2)}; \qquad (9)$$

where $D_i$ is the DML distance between two points in the N-dimensional space, with one point representing the typical instance, $x_{ti}$, as defined in the DML algorithm for the i-th class, $C_i$, and another point being an arbitrary point (or sampling vector), x, with $$D_i = \sqrt{\sum_{j=1}^{N} \frac{(x_j - x_{tij})^2}{\sigma_{ij}^2}}; \qquad (10)$$

This model is valid if all spectral components are statistically independent. This may not be true if the intrinsic color variation within the class is the dominant component, since the spectral curve is smooth and continuous, the variation of neighboring wavelength bands will most likely to be somewhat correlated.

A more general probability density may be established as a univariate function of the DML distance, such that $$p(x|C_i) = p(D_i). \qquad (11)$$

For example, it could be established from the histogram (in $D_i$) of a large number of random samples for Class $C_i$.

While the above discussions are based on continuum spectral data, the DML algorithm and equations (10) & (11) can be applied to any other multivariate data types. Of course, it is also applicable to univariate cases.

Combining Non-Spectral and Spectral Data

While the variation of different spectral components of a given class may be correlated, it is a very good assumption that the variation of data from different sources (i.e., derived from different physical attributes) are independent from each other.

For a produce recognition system, relevant non-spectral data types may include data captured from produce item 18, such as average reflectivity, size, shape, weight, color texture, spatial texture, hardness, smell, and other such factors. For example, cameras 48A and 48B provide one-dimensional texture information. Scale 34 provides weight information. All these are related to different physical properties of an object. Any combination of these properties, if sensed or measured, may be used to identify (or classify) the object.

Other important non-spectral pieces of information do not involve the physical properties of the object. For example, the check-out frequency of a given produce item can be used as a priori information for recognition. Other a priori probabilities include time of year, geographical region, total sales, and combinations thereof. Data to support calculation of these probabilities may be derived from customer shopping information. These probability values can then be used to rank the classes and to determine a subset of the most likely classes.

For any given type of data, if the data can be reduced to a single parameter, the conditional probability density is naturally a univariate function. If the data involves two or more variables, it can be reduced to a univariate function by using the DML distance, as defined in equation (10).

In more detail, assume there are $N_D$ types of data available, with each data type being projected into a one-dimensional space; let's notate the variables as $$x = \{x^{(i)}, i=1, 2, \ldots, N_D\}; \qquad (12)$$

The univariate conditional probability density for each data type can be written as $$p(x^{(i)}|C_i, i=1, 2, \ldots, N_D\}; \qquad (13)$$

Under the assumption that the variables from different data types are statistically independent from each other, the combined conditional probability density function can be defined as the product of all the individual density functions, $$p(x|C_i) = p(x^{(1)}, x^{(2)}, \ldots, x^{(N_D)}|C_i), \text{ or } p(x|C_i) = p(x^{(1)}|C_i)p(x^{(2)}|Ci) \ldots \cdot p(x^{(N_D)}|C_i). \qquad (14)$$

By applying equation (11), we have $$p(x|C_i) = p(D_i^{(1)})p(D_i^{(2)}) \ldots p(D[<m]ed_i^{(N_D)}). \qquad (15)$$

Equation (14) is called the state-conditional probability density or class-conditional probability density.

When the natural frequency (or probability of occurrence) for each class, $$f_i, i=1,2, \ldots N_C \text{ with } \Sigma f_i = 1, \qquad (16)$$

is available, the a posteriori probability for a given observation can be computed using Bayes Rule, $$P(C_i \mid x^{(1)}, x^{(2)}, \ldots, x^{(N_D)}) = \frac{p(x^{(1)}, x^{(2)}, \ldots, x^{(N_D)} \mid C_i)f_i}{\sum_{i=1}^{N_C} p(x^{(1)}, x^{(2)}, \ldots, x^{(N_D)} \mid C_i)f_i}, \qquad (17)$$

where $N_c$ is the total number of classes. This is the probability for the observed object to belong to class $C_i$, given that the available measurement is described in equation (12). With the conditional probability derived in equation (15), it may be simplified as $$P(C_i \mid x) = \frac{f_i \prod_{j=1}^{N_D} p(D_i^{(j)})}{Q}, \qquad (18)$$

with $$Q = \sum_{k=1}^{N_C} \left\{ f_k \prod_{j=1}^{N_D} p(D_k^{(j)}) \right\} \qquad (19)$$

The class with the highest probability as computed with equation (17) is the most likely class. For many decision theory applications, a unique identification is required, in which case choosing the class with the highest a posteriori probability will guarantee the lowest error rate, statistically.

However, for applications in which the error rate would be too high if only a single choice were allowed, the a posteriori probability should be used instead to provide a ranked list of possible identifications.

There are two scenarios for the application of the a posteriori probabilities:

1. Provide a ranked list of all classes. In this case, only the relative value of the probability matters and the constant factor Q in equation (18) can be ignored.

2. Provide a truncated list of the most likely classes. A ranked list of all $N_C$ classes may be truncated by setting a minimum probability value. Let's simplify the notation of the a posteriori probability as $$P_i = P(C_i | x^{(1)}, x^{(2)}, \ldots, x^{(ND)}); \quad (20)$$

if we set the minimum probability as $P_{min}$, and sort $P_i$, for all classes in descending order such that $$P_1 > P_2 > \ldots P_k \geq P_{min} > P_{k+1} > \ldots > P_{N_C},$$

thus the truncated rank-list of choices is given by the first k classes.

Figure 7:
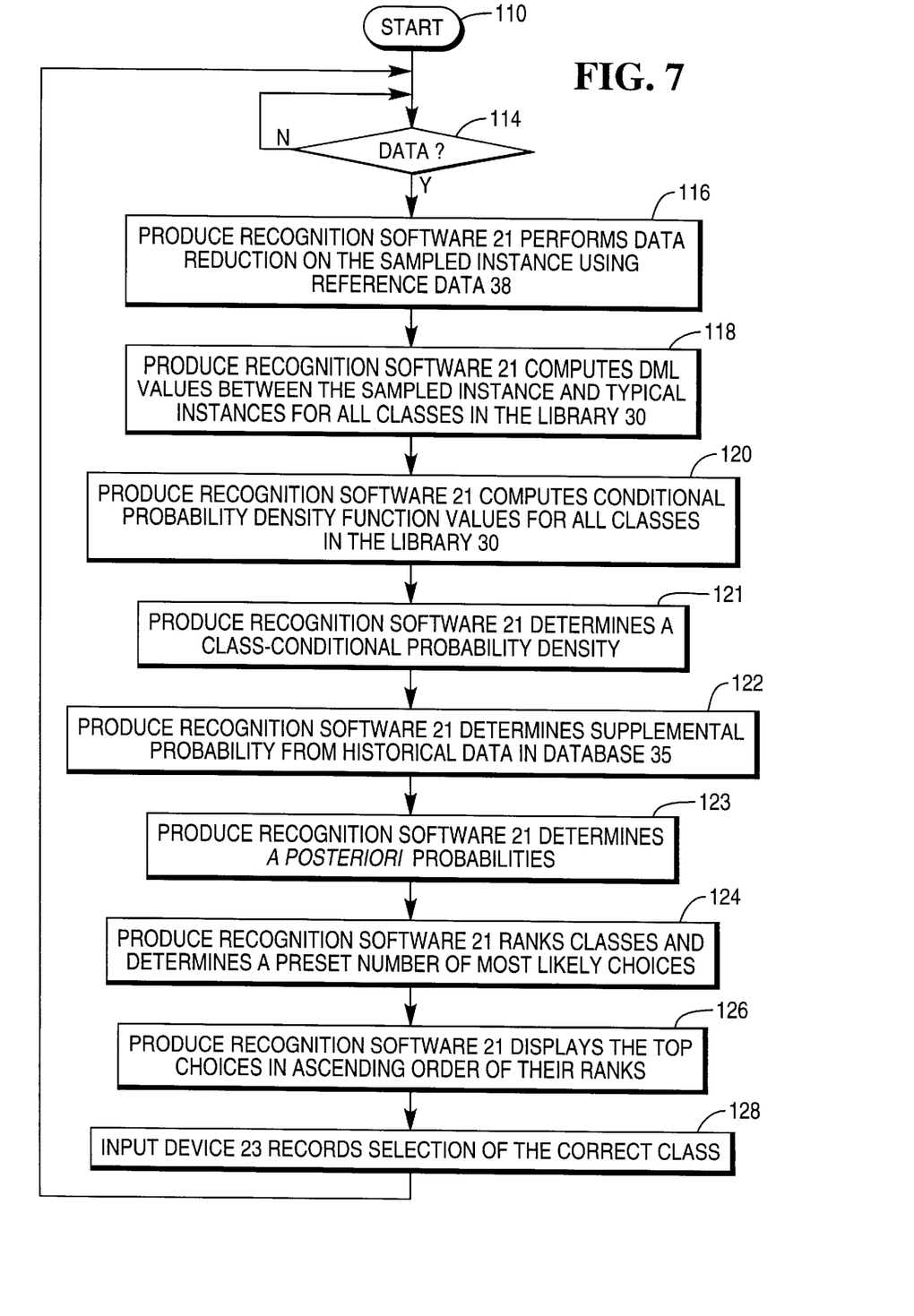
FIG. 7 is a flow diagram illustrating the recognition method of the present invention.

Turning now to FIG. 7, the produce recognition method of the present invention begins with START 110.

In step 114, produce recognition software 21 waits for spectral data from spectral data collector 14 and non-spectral data from non-spectral data collector 48. Operation proceeds to step 116 following produce data collection.

Figure 8:
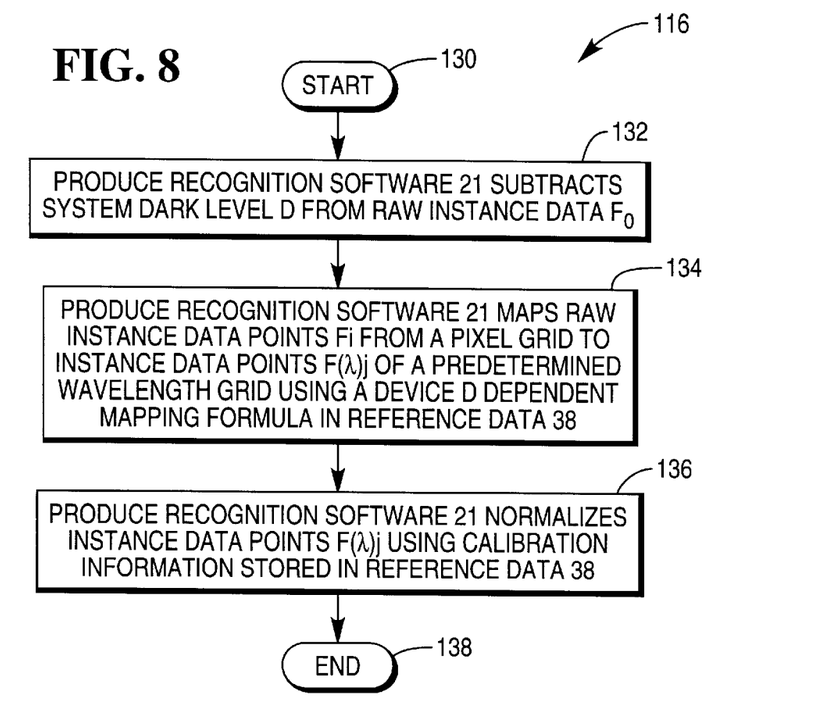
FIG. 8 is a flow diagram illustrating spectral data reduction procedures.
Figure 9:
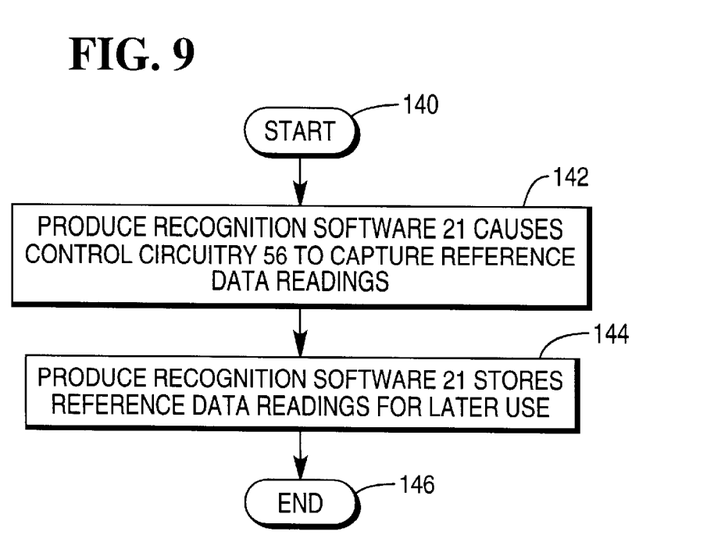
FIG. 9 is a flow diagram illustrating non-spectral data reduction procedures for a particular type of non-spectral data collector.

In step 116, produce recognition software 21 performs data reduction on the sampled instances (FIGS. 8 and 9).

In step 118, produce recognition software 21 computes DML values between the sampled instance and typical instances for all classes 36 in library 30.

In step 120, produce recognition software 21 computes conditional probability densities for each class 36 using the DML values.

In step 121, produce recognition software 21 combines the conditional probability densities to produce a class-conditional probability density.

In step 122, produce recognition software 21 determines a supplemental or a priori probability from historical data in database 35 or obtains the a priori a probability from library 30.

In step 123, produce recognition software determines a posteriori probabilities for each class, i.e., that produce item 18 belongs to a any given class 36, from the class-conditional probability density and the a priori probability using Bayes rule.

In step 124, produce recognition software 21 ranks classes 36 and determines a number of most likely choices according to a predefined minimum probability value. For example, produce recognition software 21 may choose to list only nine of the candidates due to display limitations.

In step 126, produce recognition software 21 displays the number of likely choices in order of their ranks.

In step 128, produce recognition software 21 records an operator choice for produce item 18 through touch screen 23. Transaction terminal 20 uses the identification information to obtain a unit price for produce item 18 from transaction server 24. Transaction terminal 20 then determines a total price by multiplying the unit price by weight information from scale 34 (or by quantity entered by operator from a keypad). Operation returns to step 114 to wait for another produce item.

Turning to FIG. 8, a data reduction method for spectral data used to build library 30 and process spectral produce data during a transaction is illustrated beginning with START 130.

In step 132, produce recognition software 21 subtracts the system dark level D from the raw instance data $F_0$. Dark level D is the detector reading with light source 40 off and window 60 covered. This procedure also applies to both spectral and non-spectral data.

In step 134, produce recognition software 21 maps raw instance data points $F_i$ from a pixel grid to instance data points $F(\lambda)_j$ of a predetermined wavelength grid (e.g., 400 nm to 700 nm over 5 nm intervals) using a device-dependent mapping formula in reference data 38:

$$\{F_i, i=1, N_p\} \rightarrow \{F(\lambda_j), j=1, N_\lambda\},$$

where $N_p$ is the number of pixels in the detector array 54 and $N_\lambda$ is the number of preset wavelengths. The device-dependent mapping formula is stored in reference data 38. For an LVF spectrometer, the device-dependent mapping formula is in the form $$\lambda = C_0 \times C_1 \times x,$$

where $C_0$ and $C_1$, are two constant factors.

In step 136, produce recognition software 21 normalizes instance data points $F(\lambda_j)$ using calibration information stored in reference data 38.

Calibration information includes reference spectrum $F_{ref}(\lambda)$ which is measured at various times throughout the operating life of spectral data collector 14 using an external reference:

$$F_n(\lambda) = \frac{F(\lambda)}{F_{ref}(\lambda)},$$

where $F_n(\lambda)$ is the normalized data.

Calibration information may also include a correction factor $C_{dev}(\lambda)$, if instead, spectral data collector 14 uses an internal reference and measures an internal reference spectrum $F'_{ref}(\lambda)$;

$$F_n(\lambda) = \frac{F(\lambda)}{C_{dev} F'_{ref}(\lambda)}.$$

In step 138, the process ends.

Turning to FIG. 9, a data reduction method for non-spectral data from camera 48 is described beginning with START 140.

In steps 142–144, produce recognition software 21 collects reference data. Reference readings are captured for use in normalizing data. Normally, steps 112 to 114 are performed during the initial system setup and calibration process. New reference readings may be needed when the system is changed, for example, following a re-calibration of produce data collector 14.

In step 142, produce recognition software 21 causes control circuitry 56 to capture reference data readings $R_1(x)$ and $R_2(x)$ from a flat and smooth white reference placed over window 61 using at least two lights of light source 40.

Reference data readings $R_1(x)$ and $R_2(x)$ will be taken using groups 40A and 40C, and groups 40B and 40D. The reference readings will be taken with image capture devices 48A and 48B.

Reference data $R_1(x)$ is captured with light source 40A turned on and light source 40C turned off. Reference data $R_2(x)$ is captured with light source 40A turned off and light source 40C turned on. Similarly, reference data in another dimension are taken with image capture device 48B and light source 40B and 40D.

In step 144, produce recognition software 21 stores reference data readings $R_1(x)$ and $R_2(x)$ for later use.

The method ends in step 146.

Advantageously, an analysis of DML values provides an appropriate measure for identifying produce items. The technique may be applied equally well to identify other items.

Although the invention has been described with particular reference to certain preferred embodiments thereof, variations and modifications of the present invention can be effected within the spirit and scope of the following claims. Specifically, while the DML algorithm developed in this invention was based on discussions of a special data type, spectral data, it may be applied to any data type or combination of data types with the same effect. For example, the technique may be applied to produce data from produce data collectors of other types. The instance point vector is just an abstract set of numbers, it may consist of one type or a number of different types of data: spectral data, physical dimensions, surface texture measures, weight, etc., and these data may be reduced in different ways or remapped to different spaces.

I claim:

1. A method of identifying a produce item comprising the steps of:
   (a) collecting produce data from the produce item;
   (b) determining Distance Measure of Likeness (DML) values between the produce data and reference produce data for a plurality of types of produce items;
   (c) determining conditional probability densities for all of the types of produce items using the DML values;
   (d) combining the conditional probability densities together to form a combined conditional probability density;
   (e) determining probabilities for the types of produce items from the combined conditional probability density;
   (f) determining a number of candidate identifications from the probabilities; and
   (g) identifying the produce item from the number of candidate identifications.

2. The method as recited in claim 1, wherein step (e) comprises the substeps of:
   (e-1) determining an a priori probability for the types of produce items; and
   (e-2) determining the probabilities for the types of produce items from the combined conditional probability density and the a priori probability.

3. The method as recited in claim 1, wherein step (g) comprises the substeps of:
   (g-1) displaying the number of candidate identifications; and
   (g-2) recording an operator selection of one of the number of candidate identifications.

4. The method as recited in claim 1, wherein step (a) comprises the substep of:
   collecting spectral data.

5. The method as recited in claim 1, wherein step (a) comprises the substep of:
   collecting non-spectral data.

6. The method as recited in claim 1, wherein step (a) comprises the substeps of:
   collecting spectral data from a spectrometer; and
   collecting non-spectral data.

7. A method of identifying a produce item comprising the steps of:
   (a) collecting produce data from the produce item;
   (b) determining Distance Measure of Likeness (DML) values between the produce data and reference produce data for a plurality of types of produce items;
   (c) determining conditional probability densities for all of the types of produce items using the DML values;
   (d) combining the conditional probability densities together to form a combined conditional probability density;
   (e) determining an a priori probability for the types of produce items;
   (f) determining probabilities for the types of produce items from the combined conditional probability density and the a priori probability;
   (g) determining a number of candidate identifications from the probabilities;
   (h) displaying the number of candidate identifications; and
   (i) recording an operator selection of one of the number of candidate identifications.

8. A method of combining spectral data with non-spectral data for recognizing a produce item comprising the steps of:
   (a) collecting the spectral and non-spectral data for the produce item;
   (b) determining Distance Measure of Likeness (DML) values between the spectral and the non-spectral data and reference produce data for a plurality of types of produce items;
   (c) determining conditional probability densities for all of the types of produce items using the DML values;
   (d) combining the conditional probability densities to form a combined conditional probability density; and
   (e) determining probabilities for the types of produce items from the combined conditional probability density.

9. The method as recited in claim 8, wherein step (e) comprises the substeps of:
   (e-1) determining an a priori probability for the types of produce items; and
   (e-2) determining the probabilities for the types of produce items from the combined conditional probability density and the a priori probability.

10. A produce recognition system comprising:
    a number of sources of produce data for a produce item; and
    a computer system which determines Distance Measure of Likeness (DML) values between the produce data and reference produce data for a plurality of types of produce items, determines conditional probability densities for all of the types of produce items using the DML values, combines the conditional probability densities together to form a combined conditional probability density, determines probabilities for the types of produce items from the combined conditional probability density, determines a number of candidate identifications from the probabilities, and identifies the produce item from the number of candidate identifications.

11. A produce recognition system comprising:
    a number of sources of produce data for a produce item; and
    a computer system which determines Distance Measure of Likeness (DML) values between the produce data and reference produce data for a plurality of types of produce items, determines conditional probability densities for all of the types of produce items using the DML values, combines the conditional probability densities together to form a combined conditional probability density, determines an a priori probability for the types of produce items, determines probabilities for the types of produce items from the combined conditional probability density and the a priori probability, determines a number of candidate identifications from the probabilities, displays the number of candidate identifications, and records an operator selection of one of the number of candidate identifications.

12. The system as recited in claim 11, wherein one of the sources comprises a spectrometer.

* * * * *